(12) United States Patent
Ghosal

(10) Patent No.: US 6,440,436 B1
(45) Date of Patent: Aug. 27, 2002

(54) PROCESS FOR PREPARING PURIFIED SHILAJIT COMPOSITION FROM NATIVE SHILAJIT

(75) Inventor: Shibnath Ghosal, Benares (IN)

(73) Assignees: Natreon Inc., New Brunswick, NJ (US); Indian Herbs Research & Supply Company Ltd., Saharanpur (IN)

( * ) Notice: Subject to any disclaimer, the term of this patent is extended or adjusted under 35 U.S.C. 154(b) by 0 days.

(21) Appl. No.: 09/860,890

(22) Filed: May 18, 2001

(51) Int. Cl.$^7$ .................. A01N 25/34; A01N 65/00; A61K 9/48; A61K 9/20; A61K 9/14
(52) U.S. Cl. ................ 424/401; 424/408; 424/452; 424/465; 424/485; 424/195.18; 424/725
(58) Field of Search ................... 424/195.18, 725, 424/401, 408, 452, 465, 485

Primary Examiner—Herbert J. Lilling
(74) Attorney, Agent, or Firm—Walter Katz

(57) ABSTRACT

A purified shilajit composition is provided herein from native shilajit. The composition has an abundance of bioactive components, particularly, at least 0.3%, preferably 0.4–1%, by weight, oxygenated dibenzo-α-pyrones and at least 60%, preferably 65–70%, by weight of fulvic acids of low-to-medium molecular weight ($\bar{M}n$ of 700–2000) with an $E_4/E_6$ ratio of 8–10 at $\lambda$ 465–665 nm, and whose 2% aqueous solution has a pH of $\geq 7$. Personal care, pharmaceutical and nutritional use formulations of the purified shilajit composition also are described.

9 Claims, No Drawings

PROCESS FOR PREPARING PURIFIED SHILAJIT COMPOSITION FROM NATIVE SHILAJIT

BACKGROUND OF THE INVENTION

1. Field of the Invention

This invention relates to shilajit compositions, and particularly to purified shilajit compositions obtained from native shilajit, which compositions have an abundance of defined bio-active constituents and are devoid of toxic components, and to personal care, pharmaceutical and nutritional use formulations thereof.

2. Description of the Prior Art

Rejuvenating changes in one's body can be initiated and effected by nutrition, herbs and herbo-minerals. Aging and its associated problems are a degenerative disease, which, however, is preventable and treatable. The aging process involves the action of highly reactive free radicals, produced systemically, which interact with other cellular compounds and produce oxidative damages and eventually kills cells and tissues and impairs the immune function of the organism. Such free radical damage accumulates and increases with age, creating degenerative diseases, such as Alzheimer's, cardiovascular, arthritis, cancer and over a hundred other diseases.

DNA, the cellular building block of the body, is very sensitive to oxidative stress. Although repairs to damaged DNA are constantly being made, the cell's mechanism cannot keep up with the number of mutations that occur in the organism, particularly in the aged. Mitochondria, the part of the cell that is responsible for producing cellular energy, has its own DNA, but it does not have a repair mechanism to give it protection against free radical induced damage. The mutation of mitochondrial DNA therefore produces a greater adverse effect than DNA mutation elsewhere in the system. Researchers in recent years have shown that certain individual natural supplements, such as omega-3-polyunsaturated fatty acids and metabolites thereof, oxygenated dibenzo-α-pyrones, and their O-acylesters, as well as hydroxyacetophenones and α-lipoic acids, can protect against oxidative damage to mitochondrial DNA.

Accordingly, it is desired in this invention to provide a purified composition of bioactive agents to protect the body against free radical damage.

Native shilajit is a blackish-brown exudation, of variable consistencies, obtained from steep rocks of different formations found in the Himalayas at altitudes between 1000–5000 m, from Arunachal Pradesh in the East, to Kashmir in the West. Shilajit also is found in other mountain ranges of the world, e.g. Afganisthan (Hindukush, Badakh-Shan), Australia (Northern Pollock Ranges), and in the former USSR (Tien-Shan, Pamir, Caucasus, Ural). Native shilajit is believed to arrest aging and also produce rejuvenation, two important attributes of an Ayurvedic rasayan medicine. Considerable controversy, however, has existed in the literature concerning the nature and chemical character of shilajit. It has been variously described as a bitumen (asphalt), a mineral resin, a plant fossil, a substance of mixed plant and animal origin, or an inorganic substance.

Generally, native shilajit contains two classes of organic compounds, namely, (a) humic substances and (b) non-humic organic metabolites. Humic substances are the major organic constituents of native shilajit, present in an amount of about 80–85% therein, and have molecular weights ranging from several thousands for humic acids (HAs), and up to several million for polymeric humins (HMs), to only a few hundred for its fulvic acid (FAs) component. These substances also are found in soils and sediments distributed over the earth's surface, occurring in almost all terrestrial and aquatic environments. Humic substances are produced by the interactions of plants, algae, and mosses (bryophtes), with microorganisms, by a process known as humification. Humification of latex- and resin-bearing plants is primarily responsible for the production of the water-soluble humic substances.

The non-humic substances of shilajit are low molecular weight ($M_w$) compounds of plant and microbial origin, occurring in and around shilajit bearing rocks. The remaining non-humic organic masses in shilajit comprise a mixture of low $M_w$ aromatic, aliphatic alicyclic, and heterocyclic (N-and S-containing) compounds. Of particular biological interest are low $M_w$ oxygenated dibenzo-α-pyrones (DBP) and hydroxyacetophenones (HAPs).

The biological effects of shilajit are believed to be due to the two distinct classes of bioactive compounds: (i) DBPs, both mono- and bis-compounds thereof, in free and metal-ion conjugated forms; and (ii) fulvic acids (FAs) from shilajit-humic substances, which function as a carrier for the bioactive DBPs. However, native shilajit rhizospheres from different origins suffer from the presence of only small amounts of (i) and (ii) therein. Large amounts of contaminants, e.g. high $M_w$ polymeric quinones, humins (HMs), and inorganic substances are present. Furthermore, shilajit rhizospheres are always heavily infested at its periphery with a large array of microorganisms, some of which are producers of mycotoxins. Thus, the potential risk of ingesting shilajit in its native form, or only after rudimentary purification, with no control or defined standards, is quite apparent.

The prior art in this field is described in the "Information Disclosure Statement", attached hereto. Other cumulative prior art is exemplified by the following references:

(1) S. Ghosal et al, Phytotherapy Res., 1991, 5, 211.

(2) S. Bhaumik, S. Chartopadhyay and S. Ghosal, Phytotherapy Res., 1993, 7, 425.

(3) Y. C. Kong et al, Int. J. Crude Drug Res., 1987, 25, 179.

(4) S. Ghosal, S. K. Singh and R. S. Srivastava, J. Chem. Res., 1988, 196.

(5) M. V. S. Sultanbawa, Tetrahedron, 1980, 36, 1465.

(6) S. B. Scharya et al, Indian J. Exp. Biol., 1988, 26, 775.

(7) S. Ghosal et al, Phytotherapy Res., 1989, 6, 249.

Accordingly, it is an object of this invention to provide a purified shilajit composition which is standardized with respect to its bioactive chemical components, and which is devoid of toxic materials therein.

A particular object of this invention is to provide purified shilajit compositions having an abundance of bioactive components, particularly oxygenated dibenzo-α-pyrones (DBPs), and carrier molecules, which are low-to-medium molecular weight fulvic acids (FAs) present in abundant amounts in the composition.

Another object herein is to provide personal care, pharmaceutical and nutritional use formulations containing a predetermined amount of said purified shilajit composition.

These and other objects and features of the invention will be made apparent from the following description thereof.

SUMMARY OF THE INVENTION

What is provided in this invention is a purified shilajit composition, without toxic components, obtained by extraction of native shilajit whose biologically active components are present in weight amounts of:

(a) at least 0.3%, preferably 0.4–1%, of an oxygenated dibenzo-α-pyrone (DBP), its di- and/or tetramers, and their esters; and (b) at least 60%, preferably 65–70%, of low-to-medium molecular weight Mw(M̄n) fulvic acids (FAs), (M̄n is a number average molecular weight), having an $E_4/E_6$ absorption ratio of 8 to 10 at $\lambda$ 465/665 nm.

The composition of the invention, as a 2% aqueous solution, has a pH of >7, preferably 7–8.

Preferably (a) is a methanol soluble 3-OH or 3, 8 $(OH)_2$ DBP derivative, or their $C_{16}$–$C_{22}$ acyl esters; and (b) is a water soluble FAs.

Preferably the purified shilajit composition also includes, 0.01% to 0.4% of ω-polyunsaturated fatty acids; 0.1–0.4 of a mono- or di-hydroxy-acetophenone, or $C_{16}$–$C_{22}$ acyl esters thereof; and 0.05 to 0.3% of α-lipoic acid.

Preferably, the fulvic acid component in (b) has an $E_4/E_6$ ratio of about 9–10.

Preferably, the purified shilajit composition also contains about 3–12% of benzoic acid, m-OH benzoic acid or $C_{16}$–$C_{22}$ alkanol esters thereof; and about 0.5–1% of —N and —S heterocyclic and other aromatic compounds.

The composition herein is further characterized by the substantial absence of humic acid and polymeric humins.

DETAILED DESCRIPTION OF THE INVENTION

In accordance with the invention, there is provided a purified shilajit composition, without toxic components, obtained by extraction of native shilajit whose biologically active components are present in weight amounts of:

(a) at least 0.3%, preferably 0.4–1%, of an oxygenated dibenzo-α-pyrone (DBP), its di- and/or tetramers, and their esters; and (b) at least 60%, preferably 65–70%, of low-to-medium molecular weight Mw(M̄n) fulvic acids (FAs), (M̄n is a number average molecular weight), having an $E_4/E_6$ absorption ratio of 8 to 10 at $\lambda$ 465/665 nm.

The purified shilajit of the invention includes (a) mono- or di-hydroxy or tetrameric dibenzo-α-pyrones (DBP) having the formulas shown below:

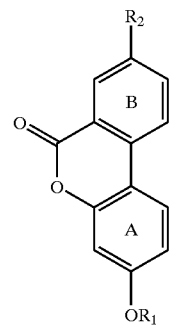

DBP
$R_1 = R_2 = H$
$R_1 = Me, R_2 = H$
$R_1 = H, R_2 = OH$

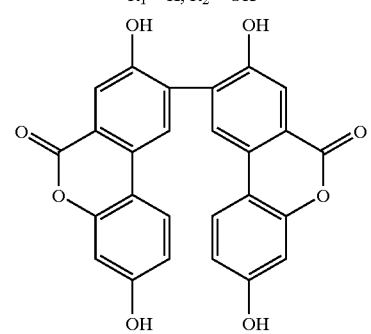

DIMERIC DBP & ITS HEMIQUINONE FORM

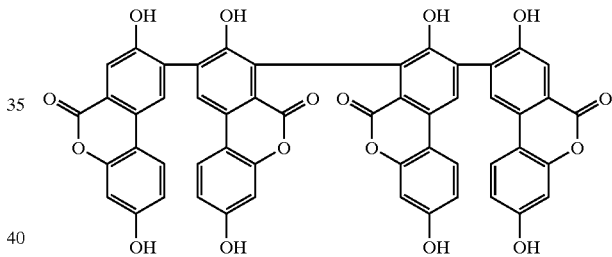

TETRAMERIC DBP & ITS HEMIQUINONE FORM and (b) fulvic acids (FAs) which have repeat units having the formula:

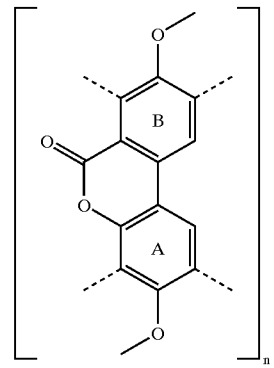

The methanol soluble portion of the purified shilajit composition also includes 0.1–0.5% 3-OH dibenzo-α-pyrone; 0.3–1.5% 3,8-diOH dibenzo-α-pyrone; 0.001–0.1% eicosapentaenoic acid; 0.005–0.01% docosapentaenoic acid; 0.01–0.3% docosahexaenoic acid; 0.1–0.2%

2-hydroxyacetophenone; 0.01–0.2% 2,4-dihydroxyacetophenone and 0.05–0.3% α-lipoic acid.

The composition of the invention finds particular application in personal care, pharmaceutical and nutritional use formulations, suitably at a use level of 0.1 to 60% by weight of the composition, preferably about 0.2 to 10% in personal care formulations.

The purified shilajit compositions of the invention are obtained by an extraction procedure from native shilajit rock exudate, as follows:

(a) powdering native shilajit exudate and dissolving it in water as solvent, (b) filtering the mixture to remove insoluble substances, (c) evaporating water from the filtrate to obtain a brown viscous residue, (d) extracting the residue with a hot organic solvent, e.g. methanol, to obtain both a soluble fraction which includes low $M_w$ bioactive phenolic compounds particularly oxygenated dibenzo-α-pyrones, and insoluble shilajit humic substances, (e) adding dilute aqueous NaOH to the insoluble shilajit humic portion to precipitate polymeric quinones, (f) acidifying the filtrate below a pH of about 3 to precipitate humic acids leaving a brown acidic solution of fulvic acids, (g) fractionating said acidic solution by passing it over activated carbon to provide a solution of low-to-medium $M_w$ fulvic acids, (h) passing the fulvic acid solution through a $H^+$ ion-exchange resin to concentrate the fulvic acids in solution, (i) evaporating the solution, and (j) combining the low-to-medium $M_w$ fulvic acids Mw 700–2000, with the low $M_w$ bioactive phenolic compounds in a suitable proportion, e.g. 9:1 by weight.

Standardization of purified shilajit compositions is controlled analytically so that the composition contains (a) at least 0.3%, preferably 0.4–1%, of oxygenated dibenzo-α-pyrones including mono- and dimers of 3,8-dihydroxy-dibenzo-α-pyrones (in free and metal ion conjugated forms) (by HPLC analysis, chemical analysis); (b) low-to-medium $M_w$ fulvic acids (Mw 700–2000) in an amount of at least 60%, preferably 65–70% (HPTLC $E_4/E_6$ analysis at different pH levels; range 8–10, preferably 9–10; and electron spin resonance spectroscopy); and with metal ions (Fe (II/III), Cu(II) and Zn (II) and Mg(II) ions in conjugated forms of (3–5%).

The 2% aqueous solution of the composition of the invention has a pH $\geq 7$. A low pH indicates the presence of substantial amounts of humic acid, humins and polymeric humus, which, accordingly, are essentially absent herein.

The thus-obtained purified shilajit composition according to the invention has the relative abundance of bioactive constituents given in Table 1 below.

TABLE 1

Relative Abundance of Bioactive Constituents in Purified Shilajit Composition

| A. | DBPS & di- or tetramers 3-OH & 3,8-$(OH)_2$ dibenzo-α-pyrrone or its esters $C_{16}$–$C_{22}$ | Hydroxy (mono-di) acetophenones, or its esters $C_{16}$–$C_{22}$ | Benzoic acid or its long chain esters $C_{16}$—$C_{22}$ | N,S,-heterocyclic & other aromatic compds |
|---|---|---|---|---|
| Amt (%) | >0.3 | 0.1—0.4 | 3–12 | 0.5–1 |
| B. | Fulvic acids | | | |
| Amt (%) | 60 | | | |

The presence of the following additional compounds (see Structures 1–8 below), and their amounts, in the purified shilajit composition of the invention, obtained in the methanol extract, have been established by comprehensive chromatographic (HPTLC, HPLC, GLC) and spectroscopic (GC-MS, NMR) analyses using specific markers. (See Table 2).

TABLE 2

| Compound (Str. No.) | Amount (%) (w/w) |
|---|---|
| EPA (1) | 0.001–0.1 |
| DPA (2) | 0.005–0.01 |
| DHA (3) | 0.01–0.3 |
| 3-OH-DBP (4) | 0.1–0.5 |
| 3,8-di-OH-DBP (5) | 0.3–1.5 |
| 2-OH HAP (6) | 0.1–0.2 |
| 2,4-di-OH HAP (7) | 0.01–0.2 |
| LA (8) | 0.05–0.3 | where:

EPA - ω-3-polyunsaturated fatty acids (str. 1); ($C_{20:5ω3}$, eicosapentaenoic acid).

DPA - ω-3-polyunsaturated fatty acid (str. 2).

DHA - ω-3-polyunsaturated fatty acid (str. 3), ($C_{22:6ω3}$, docosahexaenoic acid).

HAPs - Hydroxyacetophenones (str. 6).

LA - Alpha-lipoic acid (str. 8).

Preferably, the purified shilajit composition of the invention contains 0.01 to 0.4% of ω-3-polyunsaturated fatty acids, 0.1 to 0.4% of hydroxyacetophenone, and 0.05 to 0.3% of α-lipoic acid.

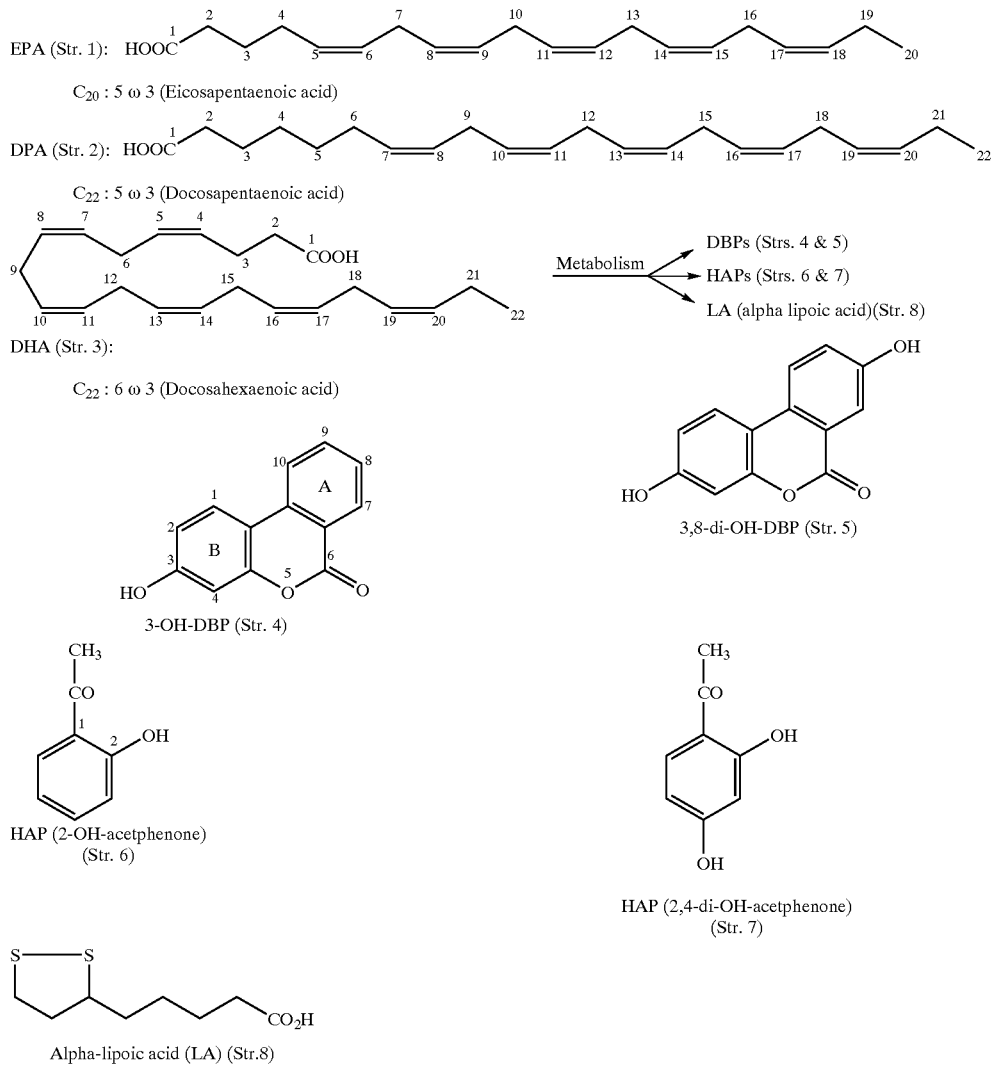

Structures (1-8): Bioactives of Purified Shilajit Composition

A typical purified shilajit composition of the invention is further characterized by the parameters given in Table 3 below.

TABLE 3

|  | Purified Shilajit Composition |
|---|---|
| Appearance | Fine powder |
| Color | Dark brown |
| Taste | Bitter |
| Odor | Characteristic |
| pH of 2% aqueous solution | 7.01 |
| Water soluble ext. value (% w/w) | 92.0 |
| Alcohol soluble ext. value (% w/w) | 26.8 |
| Total DBP (HPTLC) | 0.427% |
| % Fulvic acid | 65.3% |
| $E_4E_6$ value | 9.56 |
| Total mineral matter (Fe, Cu, Zn, Ca, Mg) | 18.48% |
| Acid insoluble mineral matter | 4.18% |

Use Formulations of Invention Composition

A. Personal Care

The formulations of Examples 1–3 below suppress skin aging due to the effects of exposure to sunlight.

EXAMPLE 1

| MOISTURIZING LOTION | |
|---|---|
| Ingredients | % (w/w) |
| Part A | |
| Stearic Acid XXX | 10.0 |
| Methyl Salicylate USP | 0.5 |
| Camphor USP | 0.5 |
| PPG-5 Ceteth-10 Phosphate | 2.0 |
| Propyl Paraben | 0.1 |
| Part B | |
| Triethanolamine | 2.0 |
| PPG-12 PEG-50 Lanolin | 2.0 |

-continued

| MOISTURIZING LOTION | |
|---|---|
| Ingredients | % (w/w) |
| Purified Shilajit Composition | 1.0 |
| Deionized Water | 82.3 |
| Methyl Paraben | 0.1 |
| | 100.00 |

Procedure

Combine ingredients of Part A with mixing and heat to 80–85° C. Combine ingredients of Part B with mixing and heat to 80–85° C. Add Part B to Part A with mixing and cool to desired fill temperature.

EXAMPLE 2

| WATER-IN-OIL COLD CREAM | |
|---|---|
| Ingredients | % (w/w) |
| Part A | |
| Mineral Oil and Lanolin Alcohol | 5.0 |
| Lanolin Alcohol NF | 1.9 |
| Aluminum Stearate, #22 | 0.1 |
| Microcrystalline Wax | 5.0 |
| Ozokerite, 170° C. MP | 2.5 |
| Mineral Oil, 70 ssu | 16.4 |
| Part B | |
| Glycerin | 1.5 |
| Purified Shilajit Composition | 0.5 |
| Magnesium Sulfate | 0.7 |
| Deionized Water | 65.8 |
| Part C | |
| Germaben II (1) | 1.0 |
| | 100.00 |

Procedure

Combine ingredients of Part A with mixing and heat to 70° C. Combine ingredients of Part B with mixing and heat to 70–75° C. Add Part B to Part A with mixing and cool to 40° C. Add Part C with mixing and cool to desired fill temperature.

EXAMPLE 3

| SKIN REJUVENATING (O/W) LOTION | |
|---|---|
| Ingredients | % (w/w) |
| Phase A | |
| Polyglyceryl-3 Methyl Glucose Distearate | 3.50 |
| Glyceryl Stearate, PEG-100 Stearate | 2.50 |
| Dicapryl ether | 5.00 |
| Coco-Caprylate/Caprate | 5.00 |
| Propylene Glycol Dicaprylate/Dicaprate | 3.00 |
| Almond Oil | 2.00 |
| Cetyl alcohol | 1.50 |
| Purified Shilajit Composition | 2.00 |

-continued

| SKIN REJUVENATING (O/W) LOTION | |
|---|---|
| Ingredients | % (w/w) |
| Phase B | |
| Glycerin | 3.00 |
| Propylene glycol | 3.00 |
| Allantoin | 0.20 |
| Methylparaben | 0.15 |
| Water, deionized | q.s. |
| Phase C | |
| Phenoxyethanol and Isopropylparaben and | 0.50 |
| Isobutylparaben and Butylparaben | |
| | 100.00 |

Procedure

Combine A, stir and heat to 65° C. Combine B, stir and heat to 65° C. Add A to B while stirring. Homogenize at moderate speeds to avoid foaming, while allowing mixture temperature to cool to 40° C. Add C, homogenize. Stir gently until mixture is homogeneous.

Example 4 below illustrates the effectiveness of the blend of the invention in enhancing the activity of sunscreen formulations.

EXAMPLE 4

| SUNSCREEN O/W SPRAY-LOTION (SPF 20) | |
|---|---|
| Ingredient | % (w/w) |
| Phase A-1 | |
| Propylene Glycol Isoceteth-3 Acetate | 5.00 |
| Octyl methoxycinnamate | 7.50 |
| Benzophenone-3 | 3.00 |
| Homomenthyl Salicylate | |
| Steareth-2 | 0.40 |
| Steareth-10 | 0.80 |
| Acrylates/$C_{10-30}$ Alkyl Acrylate Crosspolymer | 0.18 |
| Synthetic Wax | 0.80 |
| Dimethicone | 1.00 |
| Purified Shilajit Composition | 0.25 |
| Phase B | |
| Demineralized water | 50.0 qs |
| Phase C | |
| Demineralized water | 19.82 |
| Phenylbenzimdazole sulfonic acid | 1.00 |
| Propylene glycol | 2.00 |
| Triethanolamine | 0.90 |
| Propylene Glycol and DMDM Hydantoin | 1.00 |
| and Methylparaben | |
| | 100.00 |

Procedure

Combine A, stir and heat to 80° C. Heat B to 80° C. Add A to B while stirring with a propeller mixer. Continue stirring A/B for 20 minutes while maintaining the temperature between 70–75° C. Combine C, heat and stir to 45° C. until dissolved. Add C to A/B with agitation. Qs water. Gently homogenize A/B/C allowing mixture to cool to room temperature. Adjust pH to 7.1–7.3 with TEA. Use high shear spray device to dispense.

B. Pharmaceutical and Nutritional Supplements

EXAMPLE 5

PURIFIED SHILAJIT TABLETS AND CAPSULES

| Ingredient | (w/w, in %) | Quantity per tablet (mg) |
| --- | --- | --- |
| 1. Purified Shilajit Composition | 60.0 | 250.0 |
| 2. Avicel pH 101 | 20.0 | 84.0 |
| 3. Starch 1500 | 17.5 | 75.5 |
| 4. Stearic acid, N.F. (powder) | 2.0 | 8.5 |
| 5. Cab-O-Sil | 0.5 | 2.0 |

Note: The purified shilajit composition is granulated with starch paste to make it a free-flowing powder. Blend all the ingredients, except 4, for 25 min. in a blender. Screen in 4 and blend for an additional 5 min. Compress into tablets using 7/16-in standard concave tooling. Alternately, the blended material can be filled into appropriate capsules.

EXAMPLE 6

EXAMPLE 6
CHEWABLE PURIFIED SHILAJIT TABLETS

| Ingredient | (w/w, in %) | Quantity per tablet (mg) |
| --- | --- | --- |
| 1. Purified Shilajit Composition | 12.26 | 27.60 |
| 2. Sodium ascorbate, USP | 36.26 | 81.60 |
| 3. Avicel pH 101 | 17.12 | 38.50 |
| 4. Sodium saccharin, (powder), N.F. | 0.56 | 1.25 |
| 5. DiPac | 29.30 | 66.00 |
| 6. Stearic acid, N.F. | 2.50 | 5.60 |
| 7. Imitation orange Flavor | 1.0 | 2.25 |
| 8. FD & C Yellow #6 dye | 0.5 | 1.12 |
| 9. Cab-C-Sil | 0.5 | 1.12 |

Blend all the ingredients, except 6, for 20 min in a blender. Screen in 6 and blend for an additional 5 min. Compress into tablets using 7/16-in standard concave tooling.

EXAMPLE 7

"MAINTENANCE" MULTIVITAMIN TABLETS

| Ingredient | (w/w, in %) | Quantity per tablet (mg) |
| --- | --- | --- |
| 1. Vitamin A acetate (dry form 500 IU and 500 $D_2$ per mg) | 5.5 | 11.0 |
| 2. Thiamine mono-nitrate, USP | 0.8 | 1.65 |
| 3. Riboflavin, USP | 1.1 | 2.10 |
| 4. Pyridoxine HCl, USP | 1.0 | 2.10 |
| 5. 1% Cyanocobalamine (in gelatin) | | |
| 6. D-Calcium pantothenate, USP | 3.75 | 7.50 |
| 7. Purified Shilajit Composition | 33.25 | 66.50 |
| 8. Niacinamide | 11.0 | 22.00 |
| 9. DiTab | 13.1 | 26.20 |
| 10. Microcrystalline cellulose, N.F. | 25.0 | 50.00 |
| 11. Talc, USP | 3.0 | 6.00 |
| 12. Stearic acid (powder), N.F. | 1.5 | 3.00 |
| 13. Magnesium stearate, (powder), N.F. | 1.0 | 2.00 |

Blend all ingredients for 20 min in a suitable blender. Screen in 12 and blend for an additional 5 min. Compress at a tablet weight of 200 mg using 3/8-in standard concave tooling. Alternately, blended material is filled into a capsule containing 200 mg of multi-vitamins. These tablets or capsules can be used as nutritional supplements.

EXAMPLE 8

GERIATRIC FORMULA VITAMIN TABLETS

| Ingredient | (w/w, in %) | Quantity per tablet (mg) |
| --- | --- | --- |
| 1. Ferrous sulfate USP 95% Ethecal granulation | 30.00 | 250.0 |
| 2. Thiamine mono-nitrate, USP | 1.09 | 6.00 |
| 3. Riboflavin, USP | 1.00 | 5.50 |
| 4. Niacinamide, USP | 6.00 | 33.00 |
| 5. Purified Shilajit Composition (free flowing powder) | 17.45 | 96.00 |
| 6. Calcium pantothenate, USP | 0.73 | 4.00 |
| 7. Pyridoxine HCl, USP | 0.14 | 0.75 |
| 8. Cyanocobalmine, 0.1% spray dried | 0.82 | 4.50 |
| 9. AcDisol | 2.00 | 11.00 |
| 10. Stearic acid, (powder), N.F. | 2.00 | 11.00 |
| 11. Magnesium stearate, (powder), N.F. | 0.25 | 1.38 |
| 12. CeloCat | 38.52 | 211.87 |

Prepare a premix of items 2, 3, 6, 7. Mix in other ingredients except 10 and 11 and blend for an additional 5 min. Compress using oval punches (1=0.480 in., w=0.220× cup=0.040 in.) Sugar or film coat.

EXAMPLE 9

Geriatric Formula Vitamin Tablets

Example 8 was repeated except that the 25% Purified Shilajit Composition is replaced with fine crystals of ascorbic acid USP. These tablets can be used as nutritional supplements.

In summary, the purified shilajit composition of the invention includes defined bioactive compounds which impart therapeutic properties to the composition. Present in abundant amounts, the oxygenated dibenzo-α-pyrones (DBPs), particularly, 3-hydroxy and 3,8-dihydroxy DBPs, elicit the bioactivities of antioxidant, adaptogenic and immunomodulatory responses inside the system of recipients, and the low-to-medium Mw ($\overline{M}n$) (700 to 2,000) fulvic acids (FAs), having an $E_4/E_6$ ratio of 6–10, ensure the bioavailability of the DBP by acting as an efficient carrier for the DBPs.

The purified shilajit composition herein also is characterized by a minimum presence of humic acid, humins, polyphenolics, terpenoids, phytosteroids, amino acids, metal ions, moisture, mineral metallic ions and acid insoluble minerals, and the absence of toxic ingredients.

While the invention has been described with particular reference to certain embodiments thereof, it will be understood that changes and modifications may be made which are within the skill of the art. Accordingly, it is intended to be bound only by the following claims, in which:

What is claimed is:

1. A composition comprising:
   (a) at least 0.3% by weight of bioactive oxygenated dibenzo-α-pyrones (DBPs), or their esters; present as monomer, dimer and/or tetramers, including free and metal-ion conjugate forms thereof, and
   (b) fulvic acids of low-to-medium molecular weight, $\overline{M}n$ 700–2000, having an $E_4/E_6$ absorption ratio of 8 to 10 at λ465/665 nm, which ensure the bioavailability of DBPs by acting as an efficient carrier for the DBPs, which is obtained by successive extractions of native shilajit with water and an organic solvent, which substantially retains bioactive free and metal-ion conjugate DBPs in the composition, followed by adjustment of the pH of the resultant residue to substantially remove polymeric quinones and humus, and humic acids from the composition.

2. A personal care, pharmaceutical or nutritional formulation comprising the composition of claim 1 present therein in an amount of about 0.1 to 60% by weight.

3. A skin care or protection formulation according to claim 2 in the form of a lotion, cream or gel, wherein said composition is present in an amount of about 0.1–5%.

4. A pharmaceutical formulation according to claim 2 in the form of a tablet, syrup, elixir or capsule.

5. A nutritional formulation according to claim 2 which contains about 0.5 to 30% of said composition.

6. A skin care or protection formulation according to claim 2 which additionally contains a cosmetically acceptable carrier and at least one cosmetic adjuvant selected from the group of sunscreens, antioxidants, preservatives, perfumes, oils, waxes, propellants, waterproofing agents, emulsifiers, thickeners, humectants and emollients.

7. A composition according to claim 1 in which said extraction includes aqueous base adjustment of said residue to remove polymeric quinones and humus, followed by acidification of the filtrate to remove humic acids therefrom.

8. A process for producing a purified shilajit composition of claim 1 from native shilajit which consists essentially of:
   (a) treating powdered native shilajit exudates with water,
   (b) filtering to remove water-insoluble substances,
   (c) concentrating the filtrate to obtain a brown viscous residue,
   (d) treating the residue with a hot organic solvent to obtain an organic-soluble filtrate containing oxygenated dibenzo-α-pyrones (DBPs), or their esters, as monomers, dimmers and/or tetramers, in free and metal ion conjugate forms thereof, and an organic-insoluble residue,
   (e) adding aqueous base to the organic-insoluble residue to precipitate polymeric quinones,
   (f) acidifying the basic filtrate to precipitate humic acids leaving an acidic solution of fulvic acids,
   (g) fractionating said acidic solution to provide low-to-medium Mn fulvic acids, and
   (h) combining said DBPs and said fulvic acids.

9. A process according to claim 8 in which a 2% aqueous solution of said composition has a pH>7.

* * * * *